United States Patent [19]
Wijay

[11] Patent Number: 5,769,814
[45] Date of Patent: Jun. 23, 1998

[54] COAXIAL/DOUBLE LUMEN CATHETER

[75] Inventor: Bandula Wijay, Houston, Tex.

[73] Assignee: Leocor, Inc., Houston, Tex.

[21] Appl. No.: 807,865

[22] Filed: Feb. 26, 1997

Related U.S. Application Data

[63] Continuation of Ser. No. 559,413, Nov. 15, 1995, abandoned, which is a continuation of Ser. No. 221,363, Mar. 31, 1994, abandoned.

[51] Int. Cl.$^6$ .................................................. A61M 25/00
[52] U.S. Cl. .............................. 604/96; 604/280; 606/192
[58] Field of Search ................................ 604/93, 96, 103, 604/264, 280; 606/191, 192, 194

[56] References Cited

U.S. PATENT DOCUMENTS

| | | | |
|---|---|---|---|
| 4,782,834 | 11/1988 | Maguire et al. | 604/280 |
| 4,877,031 | 10/1989 | Conway | 604/96 |
| 4,884,573 | 12/1989 | Wijay et al. | |
| 4,921,483 | 5/1990 | Wijay et al. | |
| 5,137,513 | 8/1992 | McInnes | 604/96 |
| 5,147,377 | 9/1992 | Sahota | 606/194 |
| 5,205,822 | 4/1993 | Johnson et al. | 604/96 |
| 5,261,879 | 11/1993 | Brill | 604/96 |
| 5,304,134 | 4/1994 | Kraus et al. | 604/96 |
| 5,306,247 | 4/1994 | Pfenninger | 604/96 |
| 5,308,319 | 5/1994 | Ide et al. | 604/96 |
| 5,342,386 | 8/1994 | Trotta | 606/194 |
| 5,370,615 | 12/1994 | Johnson | 604/96 |
| 5,370,655 | 12/1994 | Burns | 606/194 |

FOREIGN PATENT DOCUMENTS

| | | |
|---|---|---|
| 0 440 345 A1 | 8/1991 | European Pat. Off. . |
| 654214 A5 | 2/1986 | Switzerland . |
| WO 91/08014 | 6/1991 | WIPO . |

Primary Examiner—Michael Powell Buiz
Assistant Examiner—Chalin Smith
Attorney, Agent, or Firm—Rosenblatt & Redano P.C.

[57] ABSTRACT

The present invention provides a low-profile balloon catheter which is extremely maneuverable and capable of dilating an occluded artery with minimal risk of angina. The catheter is highly maneuverable because its distal section has substantially coaxial inner and outer tubes which are in relatively tight mechanical communication at their proximal end and their distal ends are mechanically connected only via the balloon. As a result, the inner distal tube is relatively independent of the outer distal tube. The proximal section of the catheter is relatively stiff and preferably has two lumens therethrough. One lumen, which is substantially larger, is used to actively perfuse oxygenated blood, drugs, or dyes distal to the tip of the catheter at flowrates up to about 100 cc/min. Preferably, the inner surface of this first perfusion lumen has a shape at its inner surface that permits the second, smaller lumen to "nest" adjacent to and substantially within said inner surface of said first perfusion lumen. This "nesting" relationship between the two lumens maximizes the area of the proximal section that can be used for perfusion and insertion of the guidewire and inflation fluid through the second lumen. In order to provide a flexible, more maneuverable distal tip for the catheter, the first perfusion lumen is in fluid communication with an inner, substantially coaxial tube in the distal section of the catheter. This inner tube extends through an outer tube that is mechanically connected to the catheter and to the proximal end of the balloon. The inner tube extends through the balloon, which is mechanically connected to the inner tube at its distal end, and then empties the contents from the first perfusion lumen at the distal end of the catheter.

19 Claims, 1 Drawing Sheet

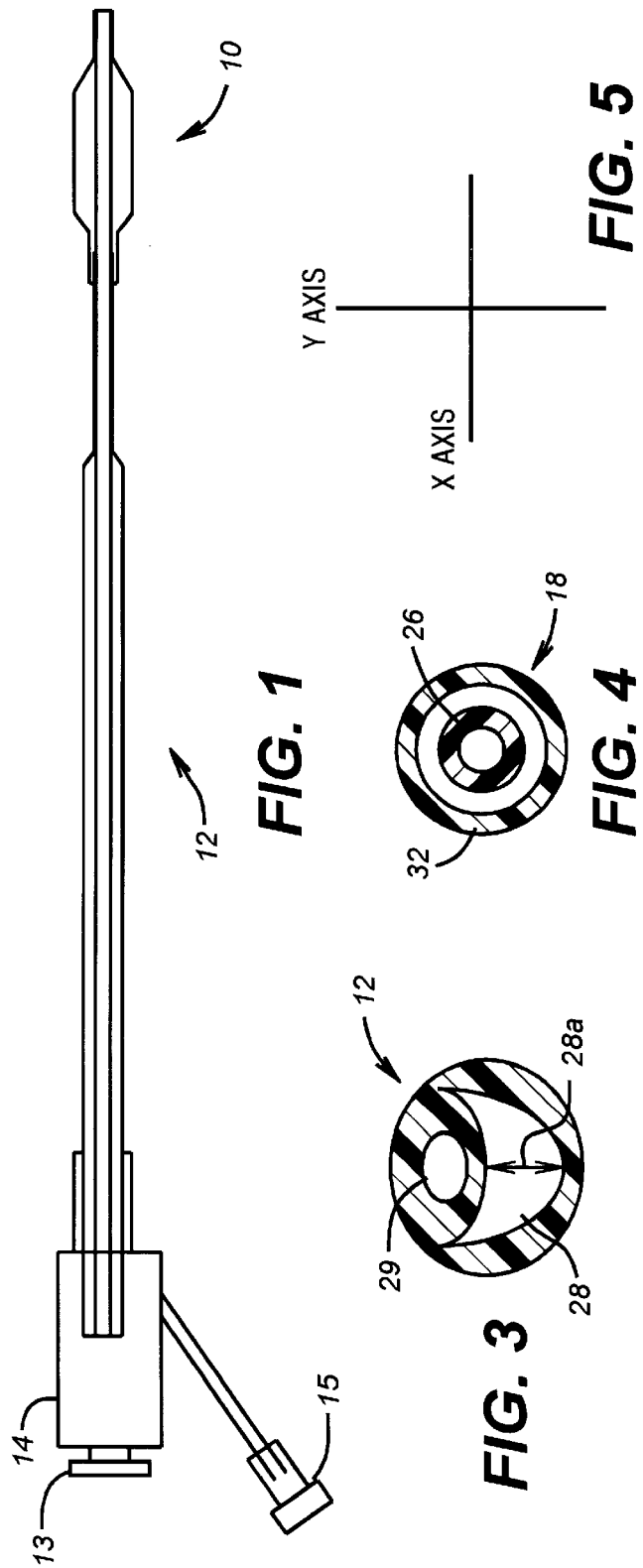

COAXIAL/DOUBLE LUMEN CATHETER

This application is a continuation of application Ser. No. 08/559,413, filed on Nov. 15, 1995, now abandoned which is a continuation of application Ser. No. 08/221,363, filed on Mar. 31, 1994, now abandoned.

FIELD OF THE INVENTION

The field of the invention relates to balloon catheter angioplasty, and more specifically to transluminal coronary angioplasty, or dilation of an obstructed vessel in a mammal. More specifically, the present invention relates to dilation of an obstructed vessel in a human with arterial occlusive disease, by a balloon catheter having a novel design.

BACKGROUND OF THE INVENTION

When a patient is afflicted with an obstructed coronary artery, the artery typically is dilated using a procedure known as percutaneous transluminal coronary angioplasty ("PTCA"). PTCA is performed using a "balloon" catheter (or a PTCA catheter). A balloon catheter consists, very basically, of an inflatable balloon and a means for guiding the balloon to the target occlusion and for inflating the balloon to dilate the artery at the point of the occlusion. Preferably, the catheter also permits simultaneous monitoring of aortic pressure and/or simultaneous dye injections to clarify the vascular anatomy.

Once it is determined that PTCA is called for, a guiding catheter typically is introduced through a sheath which guides the catheter to the aortic origin of the vessel to be dilated. A guidewire is advanced through the guiding catheter and beyond the lesion. The guiding catheter supports the balloon catheter as it is threaded onto the guidewire until the "balloon" portion of the catheter reaches the occlusion. The balloon portion then is inflated from an external port, resulting in compression of the atheromatous lesion in a manner perpendicular to the vessel, thus dilating the lumen.

Most of the available balloon catheters have two passageways or lumens. A first passageway is used to inflate and deflate the balloon with a hydraulic system. A second passageway is used to pass the guidewire through the catheter. Typically, this second passageway is large enough to maintain a channel around the guidewire to permit monitoring of the vascular pressure at the distal tip of the catheter or to permit monitoring of the vascular anatomy by radiographic dye injection.

The past few years of clinical experience have revealed that a balloon catheter system having the lowest profile is desirable in order to facilitate the passage of the balloon across severe and remote vascular obstructions. Three different catheter designs have been used to minimize the profile of the catheter. In one such design, called the "over-the-wire" system, the guidewire extends through the total length of the catheter. The advantage of the "over-the-wire" system is that the distal and proximal vascular pressure may be measured during the procedure. More specifically, the pressure differential is measured after deflating the balloon and the pressure differential is used to indicate the degree of dilation achieved.

During the angioplasty procedure, the blood flow through the target artery normally is greatly reduced, resulting in angina. As a result, it often is necessary to infuse drugs or oxygenated blood distal to the stenosis in order to maintain adequate physiological function of the target organ. Distal infusions are possible using an over-the-wire catheter if the inner lumen of the catheter is large enough to retain the guidewire and to transfer the material to be infused.

Another low-profile catheter, known as a "quick exchange" catheter, consists of a balloon at the distal end of a very stiff wire. The wire adds the strength needed for pushability and enters the catheter 15–25 cm proximal to the balloon end.

A "quick exchange" catheter has two advantages over an "over-the-wire" catheter. Sometimes, the physician conducting the angioplasty must remove the catheter and replace it with a catheter of a different size. The "quick exchange" design allows the physician to keep the guidewire in place while replacing the catheter. Also, because the guidewire only touches the catheter along a small portion of its length—compared to an "over-the-wire" catheter—relatively little force is required to move the guidewire. One disadvantage of a "quick exchange" catheter is that the catheter can neither measure distal vascular pressure nor infuse oxygenated blood, drugs, or dye distal to the balloon.

A third low-profile catheter design, known as the "balloon on the wire" design, uses a hollow guidewire with an inflatable balloon on its tip. The "balloon on the wire" design has a number of disadvantages. A "balloon on the wire" catheter can neither monitor the distal vascular pressure nor infuse oxygenated blood, drugs, or dye distal to the balloon. Also, the bulky balloon at the tip of the guidewire prevents the guidewire from being advanced and/or rotated with the same precision as a catheter that has no balloon at its tip. Finally, the inflatability of the balloon may be impaired because the balloon may twist on the wire.

Three types of perfusion have been used to minimize the risk of angina from the reduced blood flow during angioplasty: (1) passive perfusion, (2) retroperfusion, and (3) active perfusion.

In order to use passive perfusion, the catheter must be provided with a lumen having an orifice just proximal to the balloon. The lumen must extend along the balloon portion of the catheter and exit past the distal end of the catheter. When the balloon is inflated, the patient's blood pressure should force blood into the proximal orifice, through the lumen, and out of the catheter beyond the distal end of the balloon.

One of the limitations of passive perfusion is the enlarged profile of the catheter resulting from the extra lumen required adjacent to the balloon. Also, the amount of blood perfused through the catheter will depend upon the patient's blood pressure. If a patient has low blood pressure, only a very small amount of blood may be perfused.

A disadvantage of retroperfusion is that it requires the use of a separate, independent catheter to pump blood from beyond the inflated balloon.

The most advantageous type of perfusion is active perfusion. In active perfusion, the patient's blood is collected using known means and then perfused to the distal end of balloon catheter through a lumen in the guidewire. Using active perfusion, it is possible to control the flowrate of the blood through the guidewire lumen and to continue the flow of blood for more than 30 minutes. Also, the profile of the catheter is minimized because only a single lumen is required adjacent the balloon.

Other design considerations also affect the profile of the catheter. Such considerations include the required thickness of the material used to manufacture the balloon, the position of the fluorescent marker used to monitor the location of the catheter, and the need for a stiff but flexible tip on the catheter to enhance "pushability" and flexibility of the catheter.

SUMMARY OF THE INVENTION

The present invention provides a low-profile balloon catheter which is extremely maneuverable and capable of dilating an occluded artery with minimal risk of angina. The catheter is highly maneuverable because its distal section has substantially coaxial inner and outer tubes which are in relatively tight mechanical communication at their proximal end and their distal ends are mechanically connected only via the balloon. As a result, the inner distal tube is relatively independent of the outer distal tube. The proximal section of the catheter is relatively stiff and preferably has two lumens therethrough. One lumen, which is substantially larger, is used to actively perfuse oxygenated blood, drugs, or dyes distal to the tip of the catheter at flowrates up to about 100 cc/min. Preferably, the inner surface of this first perfusion lumen has a shape at its inner surface that permits the second, smaller lumen to "nest" adjacent to and substantially within said inner surface of said first perfusion lumen. This "nesting" relationship between the two lumens maximizes the area of the proximal section that can be used for perfusion and insertion of the guidewire and inflation fluid through the second lumen. In order to provide a flexible, more maneuverable distal tip for the catheter, the first perfusion lumen is in fluid communication with an inner, substantially coaxial tube in the distal section of the catheter. This inner tube extends through an outer tube that is mechanically connected to the catheter and to the proximal end of the balloon. The inner tube extends through the balloon, which is mechanically connected to the inner tube at its distal end, and then empties the contents from the first perfusion lumen at the distal end of the catheter.

BRIEF DESCRIPTION OF THE DRAWINGS

FIG. 1 is a side view of a balloon catheter according to the present invention.

FIG. 2 is a cross-sectional side view of the distal section of the balloon catheter of FIG. 1.

FIG. 3 is a cross-sectional view taken along line 3—3 in FIG. 2.

FIG. 4 is a cross-sectional view taken along line 4—4 in FIG. 2.

FIG. 5 is a diagram of the x and y axes of the catheter in relation to FIGS. 1 and 2.

DETAILED DESCRIPTION OF THE PREFERRED EMBODIMENT

The invention now will be described in detail with reference to the drawings. FIG. 1 depicts a catheter system 10, which includes a catheter made of suitable materials known in the art, having a proximal section 12 secured proximally to a fitting 14. Many suitable fittings 14 are known in the art. The particular fitting that is used with the catheter is not critical to the invention; however, the fitting must have certain features in order to be compatible with the catheter. The fitting 14 must include a mechanism 13 for inserting and maneuvering a guidewire (not shown) and for pumping perfused blood, drugs, and/or dyes through another lumen (28 in FIGS. 2 and 3) in the proximal section 12 and out the distal portion of the catheter 10. The fitting 14 also has means 15 to inflate the balloon.

The fitting 14 preferably should be insert-molded using known methods to process high-density polyethylene. Ink printing the size of the catheter and marking the inflation port will be difficult unless the fitting is appropriately surface treated. To avoid surface treating the fitting, foil printing may be used. Foil printing is reliable and economically efficient because, once the foil printing has been placed on the fitting, the printing will not come off.

The body of the catheter 10 preferably should be between about 135–140 cm long, and approximately 2 cm of this length should be housed within the fitting 14. Reinforcement may be provided along the first 2.0–2.4 cm of the proximal section 12 as it exits the fitting to provide strain relief. The proximal section 12 of the catheter 10 preferably should have a diameter of about 3.6 French. The internal structure of the proximal section 12 and the distal section 18 of the catheter 10 are shown in more detail in FIGS. 2–4.

As seen in FIG. 2, the proximal section 12 of the catheter 10 has two lumens and preferably consists of double lumen extruded tubing. As seen from the cross-section taken at A—A, shown in FIG. 3, the two lumens 28, 29 in the proximal section 12 of the catheter form a "smiley face" configuration, in which a smaller lumen 29 is nested adjacent to the inner surface of a larger lumen 28. The "smiley face" or "nested" configuration of the lumens 28, 29 (i) facilitates the maximum flow area and, therefore, the maximum volume flow of blood, drugs, dye, etc., through the "perfusion" lumen 29; (ii) in return for the lowest pressure exerted at the perfusion means 13; and (iii) allows for the lowest possible outer diameter or profile of the proximal section 12 of the catheter 10. Also, because the "perfusion" lumen 28 is relatively large and allows for active perfusion of the blood, the perfusion lumen 28 improves the operator's ability to monitor the proximal and distal blood pressure and the rate of dye or drug infusion. Finally, the web between the two lumens adds stiffness to the body, which aids in maneuvering the catheter.

Preferably, the guidewire lumen 29 should have a diameter large enough so that a suitable guidewire (not shown) will be relatively free to move within the lumen 29. The lumen also should have a diameter which will permit a sufficient amount of inflation fluid to flow to the balloon 36, but will not increase the profile of the catheter. A preferable diameter for the guidewire lumen is about 0.014 inch.

The perfusion lumen 28 may have any shape that is capable of "nesting" the guidewire lumen 29 and should be large enough to permit active perfusion of blood/fluids with flowrates up to about 100 cc/min., but small enough to maintain a low catheter profile. A preferable shape for the perfusion lumen 28 is a crescent shape, and a preferable diameter at the widest point 28a of the crescent is about 0.026–0.035 inch.

The "nested" double lumen construction of the proximal section 12 of the catheter 10 should not extend all of the way to the distal tip 18 of the catheter because double lumen tubing tends to twist when tracking through a tortuous vessel. Therefore, the catheter 10 should be provided with a distal tip 18 which has a more flexible construction so that the catheter 10 will be more maneuverable inside of the vessel. In the present invention, this is accomplished by providing the catheter with about 6–9 cm of a distal tip 18 with a substantially coaxial construction. The coaxial design feature also allows the designer to use stiffer inner tube having lubricous surface characteristics while using an outer tube more flexible so as to provide an assembly that is flexible when taken together yet stiffer in its inner construction. This flexibility in design provides means to optimize the necessary characteristics of guidewire movement for tracking and pushability.

A preferred method for accomplishing the transition from the double lumen construction of the proximal section 12 to the coaxial construction of the distal tip 18 consists of the following steps. Preferably, the proximal tip 24 of the inner coaxial tube 26 is inserted between about 3–7 mm into the distal end 22 of the perfusion lumen 28, and the outer surface of the proximal tip 24 is heat-melted to the perfusion lumen 28 using known means.

The outer coaxial tube 32 may be fixed to the distal end 22 of the proximal section 12 using any known means. Preferably, two tubes are heat-fused to connect the outer surfaces of both sections. The outer coaxial tube 32 preferably should have a diameter somewhat less than the outer diameter of the proximal section 12, but large enough to fully surround both the inner coaxial tube 26 and the second lumen 29.

Although the construction of the distal section is described as substantially "coaxial," it is not necessary for the inner tube 26 and the outer tube 32 to have x and y axes that completely coincide. As used herein, the term "substantially coaxial" means that the inner tube 26 and the outer tube 32 have x and y axes (FIG. 5) that are substantially parallel in construction, at least when the catheter is relaxed. Preferably, the y axes will substantially coincide, and the x axes will be parallel but offset from one another. However, it is possible that both the x and y axes may be offset but substantially parallel in construction. During the insertion process, the outer tube 32 may become twisted in relation to the inner tube 26 so that the x and y axes are temporarily dislocated.

Preferably, the outer diameter of the outer coaxial tube should be about 3.1 French. Decreasing the diameter of the outer coaxial tube 32 will "neck down" the distal portion 18 of the catheter and allow for additional flexibility and maneuverability. The proximal end 38 of the balloon 36 preferably should extend about 4–6 mm proximally over the distal end of the outer coaxial tube 32. The overlapping portions can be fused using any acceptable means. Preferably, the overlapping portions are heat-fused. Approximately 2–4 mm of the distal end of the balloon also should be fused to the outer surface of the distal end 40 of the inner coaxial tube 26, again, preferably by heat-melting. The coaxial arrangement of the tubes 26, 32 at line B—B is shown in cross-section in FIG. 4.

Typically, the balloon will be made of polyethylene, polyurethane, or polyester. Polyethylene and polyurethane balloons tend to have thick walls which withstand high pressures and distend considerably in response to internal pressure. A polyester balloon is preferred because it has significantly thinner walls but nevertheless will withstand high pressures and distend only minimally with increased internal pressure. The balloon may be made in a variety of sizes between about 2.0–4.0 mm.

In actual manufacture, the catheter assemblies may be stored as two subassemblies until it is known what size of balloon 36 is required. A first subassembly can be formed by fusing the inner coaxial tube 26 inside of the perfusion lumen 28 and attaching a radiopaque marker 37 to the inner coaxial tube 26 at a desired location. Typically, the radiopaque marker should be placed at a location that will be at or near the center of the balloon 36 after final assembly. This first subassembly then may be stored in stock.

Independently, the balloon 36 may be fused to the distal end 38 of the outer coaxial tube 32 and stored in stock as a second subassembly. After it is decided what size of catheter is needed, a second subassembly having a correctly sized balloon can be fused to the first subassembly, as already described. The fusing of the two subassemblies together should create a lumen 31 between the inside of the outer coaxial tube 32 and the outside of the inner coaxial tube 26. This lumen should be wide enough to permit the inflow of a sufficient amount of inflation fluid to inflate the balloon 36.

One advantageous feature of the foregoing construction is that the inner coaxial tube 26 can move somewhat independently of the outer coaxial tube 32. Therefore, even if the outer coaxial tube 32 becomes bent during the journey through the blood vessel to the target occlusion, the inner coaxial tube 26 should not become as bent as the outer coaxial tube 32. The stability of the inner coaxial tube 26 should help the catheter 10 continue to move through the vessel in spite of some bending and twisting of the outer coaxial tube 32.

Other advantages of the foregoing design are that the outer diameter and the flexibility of the distal tip 18 can be controlled. The same is not true if double-lumen extrusion tubing is tapered on a mandrel in order to "neck down" the tubing because the membrane between the two lumens 28, 29 thins out. Sizing of the inner 26 and outer 32 coaxial tubes before assembly avoids this problem and allows for control of the outer diameter of the tip 18. Also, different blends of material can be used for the inner 26 and outer 32 coaxial tubes to control the flexibility of the tip. A preferred blend of materials would be a blend of high- and low-density polyethylenes. The foregoing blend would result in an inner coaxial tube which is stiff, allowing for good guidewire movement and an outer coaxial tube which is flexible, allowing for trackability. Such control over the diameter and flexibility of the distal tip 18 would not be possible if a double-lumen proximal body was tapered to neck down the distal tip 18.

The foregoing disclosure and description of the invention are illustrative and explanatory thereof, and various changes in the size, shape and materials, as well as in the details of the illustrated construction, may be made without departing from the spirit of the invention.

I claim:

1. A catheter, comprising:

a proximal section and a distal section;

wherein said proximal section comprises a body having an inflation lumen extending therethrough for inflating a balloon and a perfusion lumen extending therethrough for active perfusion, said inflation lumen having a smaller volume capacity than said perfusion lumen and being at least partially nested within a substantially concave surface of said perfusion lumen; and wherein said distal section comprises a separate extension segment and said balloon, wherein:

said separate extension segment has flexibility for lateral movement with respect to said distal end of said body; and, said extension segment comprises a first extension lumen therethrough with a proximal end in fluid communication with said inflation lumen and with a distal end sealingly engaged with said balloon, and a second extension lumen therethrough in fluid communication with said perfusion lumen and extending through and beyond said balloon.

2. The apparatus of claim 1 wherein:

said extension segment comprises inner and outer concentric tubular sections, wherein said inner tubular section is sealingly connected to said perfusion lumen to extend said perfusion lumen beyond said balloon, and wherein said outer tubular section is sealingly connected to said inflation lumen to inflate said balloon.

3. The apparatus of claim 1, wherein:

said perfusion lumen has a generally crescent-shaped cross-section with opposed ends defining said crescent shape; and said first lumen extends into an area defined by a line drawn between said opposed ends.

4. The apparatus of claim 3 wherein:

said extension segment comprises inner and outer concentric tubular sections, wherein said inner tubular section is sealingly connected to said perfusion lumen to extend said perfusion lumen beyond said balloon, and wherein said outer tubular section is sealingly connected to said inflation lumen to inflate said balloon.

5. The apparatus of claim 3, wherein:

said first inflation lumen is substantially disposed within the area defined by a line drawn between said opposed ends of said crescent-shaped lumen.

6. The apparatus of claim 5 wherein:

said extension segment comprises inner and outer concentric tubular sections, wherein said inner tubular section is sealingly connected to said perfusion lumen to extend said perfusion lumen beyond said balloon, and wherein said outer tubular section is sealingly connected to said inflation lumen to inflate said balloon.

7. The apparatus of claim 5, wherein:

said crescent shape is formed by a pair of curved lines with a different radii meeting at two points.

8. The apparatus of claim 7 wherein:

said extension segment comprises inner and outer concentric tubular sections, wherein said inner tubular section is sealingly connected to said perfusion lumen to extend said perfusion lumen beyond said balloon, and wherein said outer tubular section is sealingly connected to said inflation lumen to inflate said balloon.

9. A catheter, comprising:

a proximal section and a distal section;

wherein said proximal section comprises a body having an inflation lumen extending therethrough for inflating a balloon and a perfusion lumen extending therethrough for active perfusion, said inflation lumen having a smaller volume capacity than said perfusion lumen and being at least partially nested within a substantially concave surface of said perfusion lumen; and wherein said distal section comprises a separate extension segment and said balloon, wherein:

said separate extension segment comprises a first extension lumen therethrough with a proximal end in fluid communication with said inflation lumen and with a distal end sealingly engaged with said balloon, and a second extension lumen therethrough in fluid communication with said perfusion lumen and extending through and beyond said balloon.

10. The apparatus of claim 9, wherein:

said extension segment is more flexible than said body.

11. The apparatus of claim 9 wherein:

said extension segment comprises inner and outer concentric tubular sections, wherein said inner tubular section is sealingly connected to said perfusion lumen to extend said perfusion lumen beyond said balloon, and wherein said outer tubular section is sealingly connected to said inflation lumen to inflate said balloon.

12. The apparatus of claim 9 wherein:

said perfusion lumen has a generally crescent-shaped cross section with opposed ends defining said crescent shape; and said inflation lumen extends into an area defined by a line drawn between said opposed ends.

13. The apparatus of claim 12 wherein said inflation lumen is substantially disposed within the area defined by a line drawn between said opposed ends of said crescent-shaped lumen.

14. The apparatus of claim 13 wherein said crescent shape is formed by a pair of curved lines with a different radii meeting at two points.

15. A catheter, comprising:

a proximal section and a distal section;

wherein said proximal section comprises a body having an inflation lumen extending therethrough for inflating a balloon and a perfusion lumen extending therethrough for active perfusion, said inflation lumen having a smaller volume capacity than said perfusion lumen and being at least partially nested within a substantially concave surface of said perfusion lumen; and wherein said distal section comprises a separate extension segment and said balloon, wherein:

said separate extension segment comprises inner and outer substantially concentric tubular sections;

said perfusion lumen extends through said inner tubular section and beyond said balloon; and, said inflation lumen extends through said outer tubular section and is sealingly engaged with said balloon.

16. The apparatus of claim 15, wherein said extension segment is more flexible than said body.

17. The apparatus of claim 15 wherein:

said perfusion lumen has a generally crescent-shaped cross section with opposed ends defining said crescent shape; and said inflation lumen extends into an area defined by a line drawn between said opposed ends.

18. The apparatus of claim 17 wherein said inflation lumen is substantially disposed within the area defined by a line drawn between said opposed ends of said crescent-shaped lumen.

19. The apparatus of claim 18 wherein said crescent shape is formed by a pair of curved lines with a different radii meeting at two points.

* * * * *